United States Patent [19]

Mers Kelly et al.

[11] Patent Number: 4,760,846
[45] Date of Patent: Aug. 2, 1988

[54] RADIAL ARTERY CLAMP

[75] Inventors: William C. Mers Kelly, Beavercreek; Robert F. Freund, Centerville, both of Ohio

[73] Assignee: Freund Medical Products, Inc., Dayton, Ohio

[21] Appl. No.: 29,218

[22] Filed: Mar. 23, 1987

[51] Int. Cl.⁴ ............................................. A61B 17/12
[52] U.S. Cl. ..................................... 128/327; 128/346
[58] Field of Search ............................. 128/325–327, 128/346

[56] References Cited

U.S. PATENT DOCUMENTS 2,079,457  5/1937  Laurisin ..................... 128/327

FOREIGN PATENT DOCUMENTS 115789  5/1918  United Kingdom ............... 128/327

Primary Examiner—Michael H. Thaler
Attorney, Agent, or Firm—Killworth, Gottman, Hagan & Schaeff

[57] ABSTRACT

An artery clamp includes a band member which is placeable around a patient's arm and a pressure pad member. The pressure pad member is mounted to the band member, and includes a first leg for applying pressure to the radial artery. The pressure pad member also includes a second leg which is disposed in a spaced relation from the first leg for stabilizing the pad member. The second leg is sufficiently small in area so as not to prevent the flow of blood through the ulnar artery in the arm of the patient.

12 Claims, 2 Drawing Sheets

RADIAL ARTERY CLAMP

BACKGROUND OF THE INVENTION

The present invention relates to a tourniquet-type device for stanching the flow of blood from a punctured vein or artery to induce hemostasis and, more particularly, to a radial artery clamp for inducing hemostasis in the radial artery of the arm.

Several tourniquets are disclosed in the patent literature. Dunton U.S. Pat. No. 37,156 discloses an adjustable tourniquet including pressure pads for arresting arterial circulation through a limb without applying pressure to other portions of a limb. Gilman U.S. Pat. No. 3,884,240 discloses a tourniquet having a U-shaped spring steel loop to which a pair of pads are mounted. A pressure screw is disposed at one end of the loop for permitting the operator to adjust the position of one of the pads.

Snow U.S. Pat. No. 4,557,262 discloses a dialysis clamp having a spring loaded pressure pad. Royce U.S. Pat. No. 4,572,182 discloses a stand-mounted artery clamp which is especially adapted for applying pressure to the femoral artery. Also of interest is Loving U.S. Pat. No. 4,314,568. Although Loving does not disclose a device for inducing hemostasis in a punctured artery, it does disclose a device for stabilizing the position of a vein prior to venipuncture, so that the clinician can insert a needle into the vein more easily.

Although the above discussed references disclose devices which are useful in performing their intended functions, all apply pressure over a relatively large area of the limb of a patient. In particular, a need exists for a device for achieving hemostasis in the radial artery of the arm upon withdrawal of a needle or intravenous tube, while permitting continued circulation through the ulnar artery.

The lower arm includes two main arteries, the radial artery and the ulnar artery which are the primary arteries for delivering blood to the lower arm and hand of a human being. The radial and ulnar arteries are companion arteries, both originating at the distal end of the brachial artery, near the elbow, and extending in a generally parallel relation along the lower arm from the elbow to the proximal part of the palm of the hand.

The radial artery may be punctured to draw blood, to perform certain blood tests, or to introduce various types of intravenous fluid into the blood stream. One test which utilizes blood drawn from the radial artery is an arterial blood gas analysis. In order to ensure accurate results, it is important to perform the blood gas analysis on the blood sample soon after the sample is drawn.

The clinician drawing the sample must ensure that hemostasis has been induced in the puncture in the radial artery before he is free to deliver the blood sample to the laboratory. Currently, hemostasis is typically induced by the clinician manually applying pressure over the puncture site for 3 to 15 minutes, however. It will be appreciated that this delay is undesirable, therefore, as the test results may be affected.

A second procedure involving the puncture of the radial artery involves the use of an indwelling intravenous line which is inserted into the radial artery. When the intravenous line is removed from the artery, pressure must be placed on the puncture site to induce hemostasis. The typical procedure requires that pressure be applied manually for about 20 to 30 minutes to the puncture site by a nurse before hemostasis is induced. Clearly, this requires an excessive amount of time for the attending nurse.

It will be appreciated that the nurse or technician would be helped greatly by a device which could be placed over the puncture site to apply pressure, thereby eliminating the need to apply pressure manually, and allowing the nurse or technician to perform other duties.

Although it is necessary to apply pressure over the puncture site to induce hemostasis, this pressure should preferably be applied selectively. Specifically, it is desirable to apply pressure over the puncture site in the radial artery, while not applying sufficient pressure over the ulnar artery to restrict the flow of blood in the ulnar artery to the lower arm and hand. For this reason, the use of prior art tourniquet devices has not been used for this procedure.

It is seen that there is a need for a device which can apply pressure over a puncture wound in a radial artery and induce hemostasis, while allowing the substantially unrestricted flow of blood through the ulnar artery.

SUMMARY OF THE INVENTION

This need is met by an artery clamp, according to the present invention, which comprises a band member placeable around an arm of a patient and a pressure pad member. The pressure pad member is mounted on the band member, and includes a first leg for applying pressure to the radial artery of the arm of a patient. The pressure pad member also includes a second leg, spaced from the first leg, for contacting the arm of the patient to stabilize the pad member. The second leg is positioned and sized so as not to apply sufficient pressure to the ulnar artery of the arm of the patient to impede the circulation of blood to the hand of the patient.

Preferably, the first and second legs each include a skin contacting surface, with the area of the skin contacting surface of the first leg being substantially greater than the area of the skin contacting surface of the second leg. The relatively large area of the skin contacting surface of the first leg facilitates the proper placement of the first leg over the puncture site, and helps to ensure that proper pressure is applied to the puncture site over a relatively broad area. The area of the skin contacting surface of the second leg is relatively smaller such that the second leg does not stop the flow of blood through the ulnar artery, even when the second leg is placed over the ulnar artery.

It is therefore an object of the present invention to provide an artery clamp having a pressure pad with a pair of spaced skin contacting legs, a first leg placeable over a puncture site to induce hemostasis in a puncture in the radial artery, and a second leg to stabilize the pad member on the arm without stopping the flow of blood through the ulnar artery.

Additional features and advantages of the present invention will become apparent to those skilled in the art upon consideration of the following detailed description of a preferred embodiment exemplifying the best mode of carrying out the invention as perceived presently.

DETAILED DESCRIPTION OF THE PREFERRED EMBODIMENT

Figure 1:
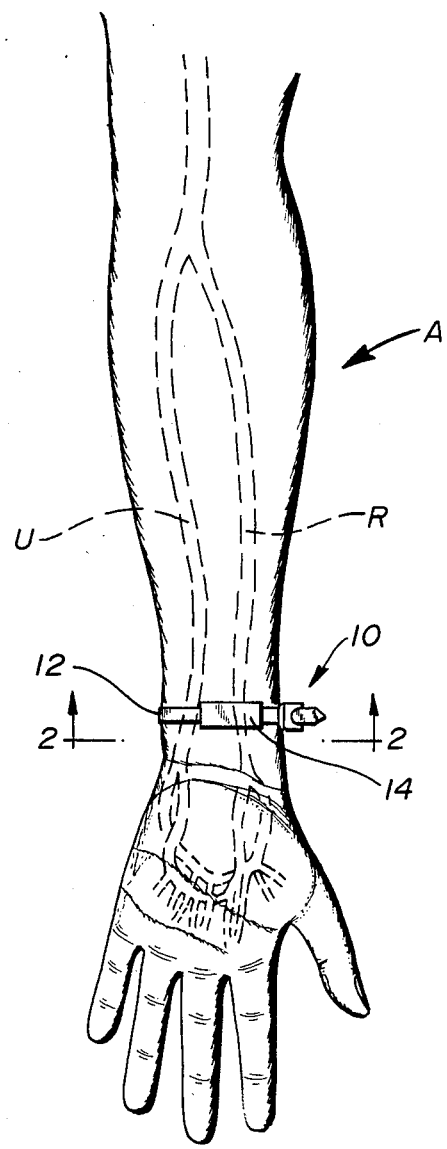
FIG. 1 is a perspective view of the artery clamp of the present invention in place on an arm of a patient showing the position of the device relative to the radial and ulnar arteries of the arm.
Figure 2:
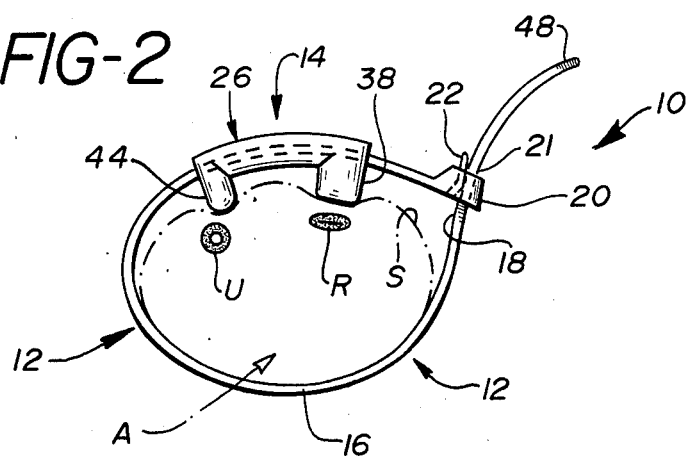
FIG. 2 is an enlarged, sectional view taken along lines 2—2 of FIG. 1.
Figure 3:
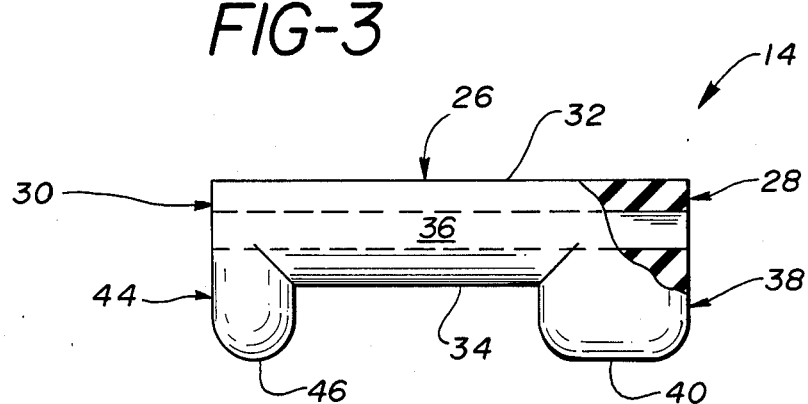
FIG. 3 is a perspective view of the pad member of the present invention.

The artery clamp 10 of the present invention is shown in the figures as including a band member 12 and a pad member 14. The band member 12 includes a strap portion 16 which, in the preferred embodiment is approximately 14 inches long. The strap portion 16 includes an array of parallel transverse ridges 18 formed on its underside surface. A buckle 20 is formed at one end of the strap portion and includes a slot 21 through which the strap portion 16 can pass. The buckle 20 also includes a tongue 22 having teeth (not shown) which engage the ridges 18 of the strap portion 16 to permit the clamp 10 to be held in place around the arm A. The tongue 22 is spring biased to bring the teeth into engagement with the ridges 18. The tongue 22 is moveable, however, for permitting the clinician to disengage the teeth from engagement with the ridges 18 for removal of the clamp 10 from the patient's arm. A band member 12, having the features and characteristics described above, which is available currently is the model PRT 4H-DU cable tie manufactured by Panduit Corporation.

The pad member 14 is mounted to the band member 12. Although the pad member 14 can be formed integrally with the band member 12, the pad member 14 is preferably molded separately, as a unitarily formed unit, from a relatively soft, resilient, clear plastic, such as Kraton D-2104, a styrene-butadiene-styrene copolymer available from the Shell Chemical Company, having a durometer hardness of between about 40 and 50 Shore A. A clear plastic is preferred to permit the clinician to view the flow of blood at the puncture site through the pad member 14.

The pad member 14 includes an elongated body portion 26 having a first end 28, a second end 30, a generally rectangular top surface 32, and a bottom surface 34. The pad member is preferably about 1.58 inches long, as measured from the first end 28 to the second end 30, and is preferably about 0.55 inches wide.

The body portion 26 of the pad member 14 defines a longitudinal opening 36, having a generally rectangular cross-section, through which the band member 12 extends. The opening 36 is sized to permit the interior walls of the opening 36 to engage frictionally the strap portion 16, thereby preventing the pad member 14 from moving relative to the strap portion 16. The strap portion 16 is inserted into the opening 36 so that when the pad member 14 is positioned on the band member 12, the first end 28 of the pad member 14 is placed closer to the buckle 20 than the second end 30. It will be appreciated that the frictional engagemenet between the strap portion 16 and the opening 36 permits the pad member 14 to be moved to different positions on the strap portion. This may be desirable to accommodate varying patient arm sizes.

The pad member 14 includes a first leg 38 disposed at the first end 28 of the pad member 14. The first leg 38 extends downwardly from the body portion 26, approximately ¼ inch below the bottom surface 34. The first leg 28 includes a generally planar skin contacting bottom surface 40, the function of which is described in more detail below. The skin contacting surface 40 of the first leg 38 has an area about 0.3 square inches. A second leg 44 is disposed at the second end 30 of the pad member 14, and extends downwardly approximately ¼ inch below the bottom surface 34 of the body portion 26. The second leg 44 includes a skin contacting surface 46 which is generally hemi-cylindrical in configuration. The area of the skin contacting surface 46 of the second leg 44 is approximately ⅓ of the area of the skin contacting surface 40, on the order of 0.1 square inches.

Preferably, the first and second legs 38, 46 are placed in a spaced relation, and are separated by a distance D, of about 0.8 inches. The spacing between the first and second legs 38, 44 and the relative small area of the skin contacting surface 46 of the second leg cooperate to prevent complete restriction of the flow of blood through the ulnar artery.

As discussed above, the radial artery R and ulnar artery U extend in the lower arm of a patient in a generally spaced parallel relation. The actual spacing between the radial and ulnar arteries will also vary along the length of the arm, and will vary between patients. For example, the spacing between these arteries is generally greater in larger persons than in smaller persons. Due to the relatively small area of the surface 46 it is unlikely that surface 46 will directly overlie the ulnar artery U when the skin contacting surface 40 of the first leg 38 is placed over the radial artery R. Additionally, the skin contacting surface 46 of the second leg 44 is sufficiently small so that even in those situations wherein the surface 46 does overlie the ulnar artery U, the flow of blood in the ulnar artery will not be blocked completely, thereby permitting the ulnar artery to carry blood to the hand of the patient during the time in which the flow of blood through the radial artery is diminished. Finally, due to the fact that the leg 38 is closer to the buckle 20, a greater downward force is applied to the pad member 14 at end 28.

The clamp 10 is utilized as follows. The strap 16 is placed loosely around the patient's arm so that the first and second legs 38, 44 extend inwardly toward the skin of the arm. The strap 16 is inserted through the slot 21 so that the teeth of tongue 22 engage the ridges 18 of the strap 16. The clamp 10 should be placed close to, but not over the puncture site, and should be placed around the arm A sufficiently loosely to permit the clamp to be moved into position over the puncture site when necessary. Preferably, the above steps are performed prior to the removal of the hypodermic needle or intravenous tube from the patient's artery.

Immediately after the removal of the tube or needle from the radial artery, the clamp 10 is moved into position over the puncture site, with the skin contacting surface 40 of the first leg 38 placed directly over the puncture site. The strap portion 16 is then pulled through slot 21 to tighten the band member 12 around the arm until the skin contacting surface 40 of the first leg 38 exerts a sufficient amount of pressure onto the puncture site to stop the flow of blood. As the pad member 14 is made preferably from clear plastic, the clinician can visually determine whether the first leg 38 is applying sufficient pressure to stanch the flow of blood at the puncture site, and to thereby induce hemostasis. It will be appreciated that as the band member 12 is tightened on the patient's arm, a point is reached beyond which the strap portion 16 does not slide freely over the skin. Further tightening of the band member results in the application of a greater force to the end of the pad 14 adjacent the buckle 20 than to the opposite end of the pad.

When the clamp 10 is properly tightened around the arm A, the skin contacting surface 46 of the second leg 44 frictionally engages the skin, preventing movement of the skin contacting surface 40 of the first leg 38, and thereby maintaining the skin contacting surface 40 over the puncture site. Additionally, leg 44 stabilizes the pad 14 in position, eliminating any twisting force which might otherwise be applied to a narrower pad by the band member 12. When properly adjusted, the clamp 10 will continue to maintain pressure over the puncture site until such time as it is removed from the patient's arm. As the skin contacting surface 46 of the second leg 44 prevents any substantial movement of the pad member 14, the clinician is free to deliver a blood sample drawn from the radial artery to the laboratory, or to perform other duties as necessary.

If the free end 48 of strap portion 16 extends through the buckle 20 by an excessive distance such that it interferes with movement of the patient's arm, end 48 may be inserted into opening 36 above the part of the strap portion 16 which extends completely through the opening 36. This insures that the end 48 will not inadvertently strike the patient's eye, for example.

To remove the clamp 10, the clinician moves the tongue 22 so that the teeth of the tongue 22 become disengaged from the ridges 18 of the strap portion 16, thereby permitting the strap portion 16 to be removed from the buckle 20. As the device can be made relatively inexpensively due to its simplicity, it can be disposed of after a single use.

In the manner described above, artery clamp 10 provides pressure over a puncture site in an artery, such as the radial artery, to stanch the flow of blood from the artery and induce hemostasis without otherwise constricting the flow of blood, while permitting the clinician to perform other tasks as the hemostasis is achieved.

Having described the invention in detail, and by reference to the preferred embodiments thereof, it will be apparent that modifications and variations are possible without departing from the scope of the invention defined in the appended claims. For example, if desired the band member 12 and the pad 14 may be unitarily formed in a molding operation.

What is claimed is:

1. An artery clamp comprising:
   a band member, placeable around the arm of a patient, and,
   a pressure pad member, mounted on said band member, said pressure pad member including
   a first leg for applying pressure to the radial artery of the arm of a patient, and
   a second leg, spaced from said first leg, for contacting the arm of the patient to stabilize said pad member, said second leg being disposed and sized so as not to apply sufficient pressure to the ulnar artery of the arm of the patient to totally block the flow of blood therethrough, said first and second legs each defining a skin contacting surface, the area of the skin contacting surface of said first leg being substantially greater than the area of the skin contacting surface of said second leg, whereby circulation of blood to the hand of the patient is maintained.

2. The artery clamp of claim 1 wherein the area of said skin contacting surface of said first leg is approximately three times greater than the area of said skin contacting surface of said second leg.

3. The artery clamp of claim 1 wherein the area of said skin contacting surface of said first leg is about 0.3 square inches and the area of said skin contacting surface of said second leg is about 0.1 square inches.

4. The artery clamp of claim 1 wherein said pad member defines an opening for receiving said band member.

5. The artery clamp of claim 4 wherein said opening is sized and shaped for snugly receiving and frictionally engaging said band member, thereby resisting movement of said pad member along said band member.

6. The artery clamp of claim 1 wherein said first leg and said second leg are spaced apart by approximately 0.8 inches.

7. The artery clamp of claim 1 wherein said pad member is comprised of a generally clear plastic material.

8. The artery clamp of claim 1 wherein said pad member is comprised of a generally clear plastic material having a hardness of between about 40 and 50 Shore A.

9. The artery clamp of claim 1 wherein said pad member comprises a unitarily formed plastic pad member.

10. The artery clamp of claim 1 wherein said band member includes a buckle means, and said pad member is mounted to said band member so that said first leg is disposed closer to said buckle means than said second leg.

11. An artery clamp comprising
    a band member placeable around an arm of a patient, and
    a resilient, unitary pressure pad member having a first end and a second end, and defining an opening for receiving said band member, said opening being sized to frictionally engage said band member to resist movement of said pad member on said band member, said pad member including
    a downwardly extending first leg, disposed adjacent said first end of said pad member, said first leg including a skin contacting surface for applying pressure to the radial artery of the patient, and
    a downwardly extending second leg disposed adjacent said second end, in a spaced relation from said first leg, said second leg including a skin contacting surface for applying pressure to the arm of the patient to prevent movement of said pad member relative to the arm while permitting the flow of blood in the ulnar artery of the patient, said skin contacting surface of said second leg being substantially smaller than said skin contacting surface of said first leg.

12. The artery clamp of claim 11 in which said pad member is formed of a generally transparent plastic material.

* * * * *